United States Patent [19]

Smakman

[11] Patent Number: 4,897,200

[45] Date of Patent: Jan. 30, 1990

[54] MACROMOLECULAR CARBONYL GROUPS CONTAINING MATERIAL SUITABLE FOR USE AS SORBENT FOR NITROGEN COMPOUNDS

[75] Inventor: Robert Smakman, Nigtevecht, Netherlands

[73] Assignee: Organon Teknika bv, Boxtel, Netherlands

[21] Appl. No.: 930,943

[22] Filed: Nov. 10, 1986

Related U.S. Application Data

[63] Continuation of Ser. No. 586,375, Mar. 5, 1984, abandoned.

[30] Foreign Application Priority Data

Mar. 23, 1983 [NL] Netherlands ............................ 8301035

[51] Int. Cl.$^4$ .............................................. B01D 15/04
[52] U.S. Cl. ................................. 210/692; 525/337.2; 525/343; 525/383; 525/386
[58] Field of Search ......................................... 210/692

[56] References Cited

U.S. PATENT DOCUMENTS

| | | | |
|---|---|---|---|
| 3,933,753 | 1/1976 | Kuntz et al. | 210/692 |
| 4,012,317 | 3/1977 | Kuntz et al. | 210/692 |
| 4,092,243 | 5/1978 | Neuray et al. | 210/692 |
| 4,178,241 | 12/1979 | Sullivan et al. | 210/692 |
| 4,502,976 | 3/1985 | Heller | 528/303 |

FOREIGN PATENT DOCUMENTS 2020996 3/1979 United Kingdom .
2051795 1/1981 United Kingdom .

*Primary Examiner*—Joseph L. Schofer
*Assistant Examiner*—Bernard Lipman
*Attorney, Agent, or Firm*—Louis A. Morris

[57] ABSTRACT

A carbonyl groups containing macromolecular material which is suitable for use as a sorbent for ammonia, urea or amino compounds. It contains structural units having 3 or more, optionally hydrated vicinal carbonyl groups, preferably keto groups, the C-atoms of which may form part of a ring structure. Particularly, the ring structure contains 5-7 C-atoms, and at least 2 ring atoms may form part of an aromatic ring system. The starting material used may be made of a polymer of the same type as that used in the manufacture of ion exchange resins. The carbonyl group containing unit may form part of an independent compound, e.g., ninhydrin which may be physically bonded to the macromolecular material, but is preferably covalently bonded thereto.

5 Claims, 1 Drawing Sheet

MACROMOLECULAR CARBONYL GROUPS CONTAINING MATERIAL SUITABLE FOR USE AS SORBENT FOR NITROGEN COMPOUNDS

This is a continuation of application Ser. No. 586,375, filed Mar. 5, 1984, now abandoned.

BACKGROUND OF THE INVENTION

The invention relates to a carbonyl groups-containing material and the preparation thereof, and to a process for compounding preparations from said material and the shaped products thus obtained. Macromolecular carbonyl groups-containing compounds for the removal of nitrogen compounds from aqueous fluids are disclosed in German Patent Application No. 23 05 186. The compounds proposed in it are alkenyl aromatic polymers having 0.01 to 1 functional α-ketoaldehyde group per aromatic ring. These compounds particularly serve to remove urea from the dialysis or ultrafiltration liquid in artificial kidneys. The use of a glyoxyl groups-containing styrene polymer is stated to result in the removal from an aqueous 1M-urea solution of a maximum amount of 61.5 g of urea per kg of polymer in a period of 15 hours.

However, this urea sorption is attained under non-physiological conditions, both as regards urea concentration (about 30 g/l instead of the concentration of 2 g/l in hemodialysis) and pH (pH=10 instead of the physiologically normal pH=7.4). If this known sorbent is used at a urea concentration of 1 g/l and pH=7, a situation which is a nearer approach to physiological conditions, then in 15 hours per kg of sorbent only 4.7 g of urea are fixed, as is given in Example 12.

Other known compounds for the removal of urea from dialysis liquid or blood plasma are described in British Patent Application 2 020 996. They are compounds with aldehyde groups activated and masked by a proton-containing substituent of the second order. The compounds may be sorbed on, for instance, activated carbon.

An experiment was carried out with 100 ml of dialysis liquid to which 10 mmoles of 2-carboxy benzaldehyde and 10 mmoles of urea (6 g/l) had been added. After 3 hours' stirring at 40° C. a decrease in urea concentration of up to about 53% of the initial concentration was measured. Also this value, however, is obtained under non-physiological conditions (pH=4.3, high urea concentration, soluble urea binder).

OBJECTS OF THE INVENTION

The present invention has for its object, int.al., to provide a sorbent for nitrogen compounds, more particularly for urea, which displays a more effective sorption under physiological conditions, i.e. by using the same amount of sorbent in the same time a larger amount of the compound to be sorbed is taken up.

SUMMARY OF THE INVENTION

The macromolecular material is characterized according to the invention in that it is a material with groupings containing three or more vicinal carbonyl groups or a hydrate thereof. It is preferred that the material should have groupings containing three vicinal carbonyl groups or a hydrate thereof. For the sake of convenience the grouping containing three or more vicinal carbonyl groups is referred to hereinafter as polycarbonyl unit.

DESCRIPTION OF THE PREFERRED EMBODIMENTS

Figure 1:
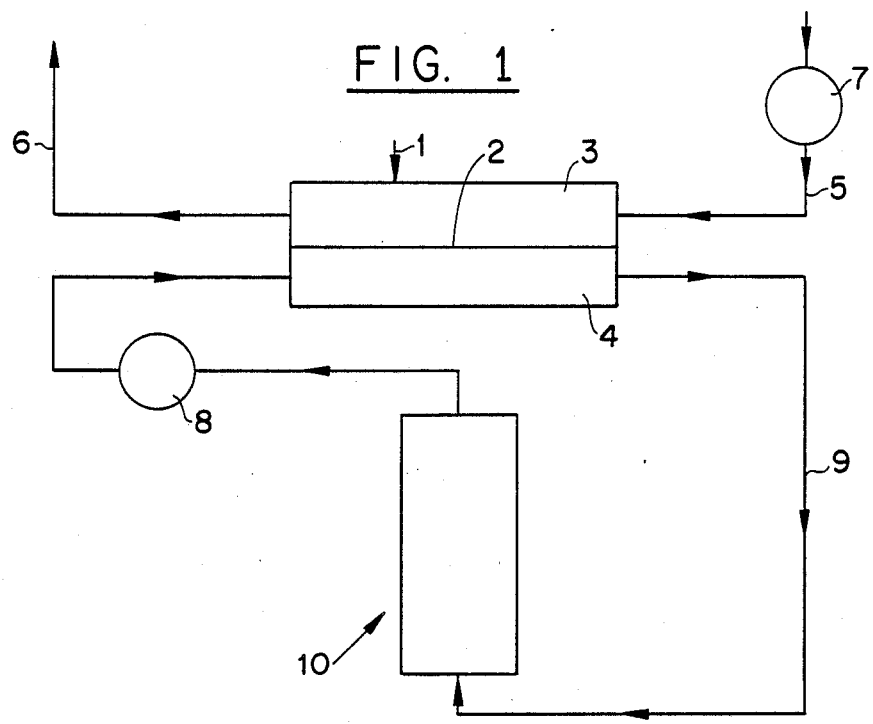

The carbon atoms of the polycarbonyl unit may form part of non-cyclic structural unit, but are preferably included in a ring. The material generally contains only one of the two types of polycarbonyl units, but it also may contain both types at once.

When the carbon atoms of the carbonyl unit are included in a ring, each ring will generally contain 5 to 7, preferably 5 carbon atoms. Generally, the ring may be homo- or heterocyclic. Preferably at least 2 carbon atoms form part of an aromatic ring system.

The material may be of a discretionally chosen chemical composition. It may be prepared for instance by the route of suitable conversions from (a) a (co) polymerisate of an ethylenically unsaturated compound, by preference of an aromatic vinyl monomer, or (b) a polycondensate, by preference of one or more aromatic components obtained, for instance, by a Friedel Crafts reaction, or (c) a natural macromolecular material, or a modified natural macromolecular material, or (d) a macromolecular material such as carbon or some other macromolecular product prepared by pyrolysis or an inorganic material such as silica, alumina, zeolites or sodium aluminum silicates. The material may have a relatively high internal surface area.

In the preparation of the polymeric material use may be made of a monovinyl aromatic compound such as styrene, vinyl toluene, vinylethyl benzene, vinyl naphthalene or vinyl anisole, or mixtures of the above-envisaged compounds. It is preferred that use should be made of styrene. In addition to or instead of monovinyl aromatic compounds one or more other monomers may be used, such as acryl compounds, for instance: acrylonitrile or methacrylonitrile, and/or acrylic acid or methacrylic acid esters. It is preferred that the material should be cross-linked. To that end the material may be prepared in the presence of a cross-linking monomer during polymerization, for instance in an amount of up to 90% by weight, based on the total amount of monomers. Alternatively, the polymer may be cross-linked after polymerization, for instance by a Friedel Crafts reaction after haloalkylation or by means of electromagnetic radiation or accelerated electrons. As cross-linking monomer there is used a compound having at least two ethylenically unsaturated groups, for instance: 1,3-butadiene, isoprene or vinyl methacrylate, but preferably di- or polyvinyl aromatic compounds such as divinylethyl benzene, trivinyl benzene and more particularly technical divinyl benzene (e.g., 60% by weight of divinyl benzene and 40% by weight of ethyl styrene). More particularly, it is preferred that use should be made of a copolymer of a monovinyl aromatic compound and a di- or polyvinyl aromatic compound. It is preferred that the material should contain 0.1 to 90% by weight of divinyl benzene. Optionally, the material may contain hydrophylic and/or ion exchanging groups for special purposes such as ion exchanging (e.g. for removal of potassium), controlling the degree of acidity, or increasing accessibility in aqueous systems. To that end there may be present strongly acid or weakly acid groups or salts thereof, strongly basic or weakly basic groups or salts thereof, and/or hydroxyl groups. Such materials may optionally be pre-charged with, for instance, (earth) alkali(ne) metal ions, such as sodium ions, potassium ions, calcium ions and/or magnesium ions, and/or chloride ions, bicarbonate ions and/or acetate ions.

The material may be prepared in any convenient manner, for instance by suspension polymerization of one or more monomers at temperatures generally in the range of 10° to 160° C. in the presence of a radical initiator, for instance: benzoyl peroxide, lauroyl peroxide, cumene hydroperoxide and/or N,N'-azobisisobutyronitrile. The material may be macroporous. To that end polymerization may optionally be carried out in the presence of one or more compounds which are capable of precipitating and/or solvating the polymer to be prepared, for instance: hexane, heptane, cyclohexane, amyl alcohol, cyclohexanol, benzene, toluene and/or chlorobenzene. Alternatively, a linear polymer, such as polystyrene, may be dissolved in the monomeric compound(s) and be extracted after polymerization. It is preferred that the macroporous material should have a macroporosity of at least 0.05 ml/g, measured by mercury porosimetry.

Matrices also can be obtained by polycondensation reactions, for instance by condensation of benzyl chloride, optionally in the presence of xylylene dichloride under the influence of a Friedel Crafts catalyst, e.g. $FeCl_3$ in, for example, an inert solvent such as nitrobenzene.

According to the invention the polycarbonyl unit may be physically attached to the material, i.e. the polycarbonyl unit forms part of a compound, such as ninhydrin, which is physically sorbed on the material. In that case it is preferred that the material should contain at least 10% by weight of ninhydrin. Further, the products according to the invention may be obtained by steric occlusion of low molecular weight vicinal tri- or polycarbonyl compounds between the chains or in the cavities of the material. Alternatively, ionic polycarbonyl compounds may be ionically attached to the material. It is preferred, however, that the polycarbonyl units should be covalently bonded to the material.

Materials having covalently bonded polycarbonyl units may be prepared in various ways, for instance by starting from a macromolecular material containing a repeating unit having at least one carbonyl group. When use is made of a material having two carbonyl groups per repeating unit, it is preferred that use should be made of a macromolecular material having repeating 1,3-dicarbonyl structural units. By preference the carbon atoms of the carbonyl groups are linked to an aromatic ring system. To obtain the polycarbonyl units it is general practice that the methylene groups adjacent to the carbonyl groups are oxidized. Oxidation may be effected by halogenation, more particularly by a bromination, followed by a treatment with a dialkyl sulphoxide. Oxidation is preferably carried out by means of a mixture of a dialkyl sulphoxide, such as dimethyl sulphoxide, and a halogen acid, such as hydrobromic acid.

As other feasible methods of oxidation may be mentioned a treatment with selenium dioxide and catalytic oxidation with air or pure oxygen under the influence of, say, metal halides, such as bromides of cobalt and/or manganese. An alternative method consists of a treatment with nitrite esters, nitrous acid or nitroso compounds, followed by hydrolysis.

A suitable, specific method of preparation comprises the following steps:

1. a macromolecular material with aromatic ring systems is reacted with an acid halide containing 3–5, preferably 3, carbon atoms;
2. the resulting carbonyl compound is in accordance with the Willgerodt or Willgerodt-Kindler reaction with sulphur and ammonia and/or an amine at a temperature between 50° and 250° C., preferably between 80° and 220° C., converted into an amide;
3. the amide obtained is hydrolysed;
4. the carboxylic acid thus prepared is directly cyclized with the aid of, for instance, polyphosphoric acid or after conversion into the acid halide cyclized by means of a Friedel Crafts reaction; after which
5. the cyclized product prepared is oxidized with the aid of one of the afore-mentioned oxidizing agents to give the material with polycarbonyl units.

Another suitable method or preparing a material having covalently bonded polycarbonyl units consists in that:

1. a macromolecular material with aromatic ring systems is acylated with a ω-halogen carboxylic acid halide containing 3–5, preferably 3, carbon atoms;
2. the halide prepared is cyclized, for instance using a strong acid such as sulphuric acid and
3. the cyclized product is oxidized with the aid of one of the aforementioned oxidizing agents to give the material with polycarbonyl units.

A third method suitable for the preparation of the material according to the invention consists in that:

1. a macromolecular material with aromatic ring systems is reacted with a 1,3-dihalogen acetone, preferably a 1,3-dichloroacetone, preferably in the presence of a Friedel Crafts catalyst and
2. the product thus prepared is oxidized using the aforementioned oxidizing agents to give the material with polycarbonyl units.

In the methods mentioned above the starting material is preferably a copolymer of styrene and technical divinyl benzene.

A polymeric, aromatic-aliphatic, linear polycarbonyl compound may be obtained as follows: in accordance with E. C. Chapin et al., Journal of Applied Polymer Science, 1982, 27, pp. 811–820, p-vinyl acetophenone is subjected to condensation with ethyl acetate; the resulting polymer with a 1,3-dicarbonyl grouping is (co)polymerized and subsequently oxidized. Alternatively, a matrix with aromatic rings may be brought into reaction with diketene using a Friedel-Crafts catalyst, followed by oxidation of the resulting 1,3-dicarbonyl groupings.

A purely aliphatic, linear, polymeric, vicinal triketo compound may be obtained for instance as follows: First a corresponding monomer is prepared containing 1,3-dicarbonyl groups, for instance methacroylacetone, by condensation of methylmethacrylate and acetone with sodium methoxide (Ph. Teyssie, G. Smets, Makromol. Chem. 1958, 26, pp. 245–251). This reaction is followed by (co)polymerization and oxidation. Also cycloaliphatic, polymeric, vicinal triketo compounds may be prepared. Thus, a polymeric cyclic 1,3-dicarbonyl compound may be obtained by conversion of maleic anhydride (co)polymer with isopropenyl acetate under the influence of a Friedel Craft catalyst followed by acid hydrolysis; and oxidation of the compound obtained results in the corresponding vicinal triketone. The same kind of conversions may be carried out with (co)polymers of maleic acid or fumaric acid or derivatives thereof.

For preparing a macromolecular compound in which the polycarbonyl groups form part of a ninhydrin structure use may optionally be made of 4-vinylphthalic ester. Its preparation is described by Tahan and Zilha in Israel J. Chem., 1971, 9, pp. 191–200. It is effected by Diels-Alder condensation of 2-ethyl butadiene and dichloromaleic anhydride, dehydrogenation, esterification, α-bromination and splitting off of HBr. The product obtained may then for instance be polymerized (or copolymerized, with, say, divinyl benzene), and the ninhydrin synthesis be carried out via condensation with dimethyl sulphoxide, or the ninhydrin synthesis may be carried out before polymerization.

The invention also relates to a macromolecular material with groupings of three or more vicinal carbonyl groups or a hydrate thereof as sorbent for ammonia, urea, creatinine or some other compound having one or more amino groups. Also compounds with thiol or alcohol groups may be taken up by the products according to the invention.

The invention also relates to a process for the compounding of preparations for reducing the urea or ammonia level by bringing a macromolecular material with groupings containing three or more vicinal carbonyl groups or a hydrate thereof in a form suitable for oral administration, and to the resulting shaped product suitable for oral administration, Said shaped product may optionally be provided with a semi-permeable wall. Tests in cell cultures carried out on such products showed absence of toxicity.

After its use as sorption agent the material according to the invention may at least partly be restored to its original state, if desired, by regenerating it with an acid solution, such as dilute sulphuric acid, at elevated temperature, for instance at about 100°–140° C.

The invention will be further described with reference to the accompanying drawing. In it are schematic representations of an hemodialysis device (FIG. 1), and a hemofiltration device (FIG. 2).

Figure 2:
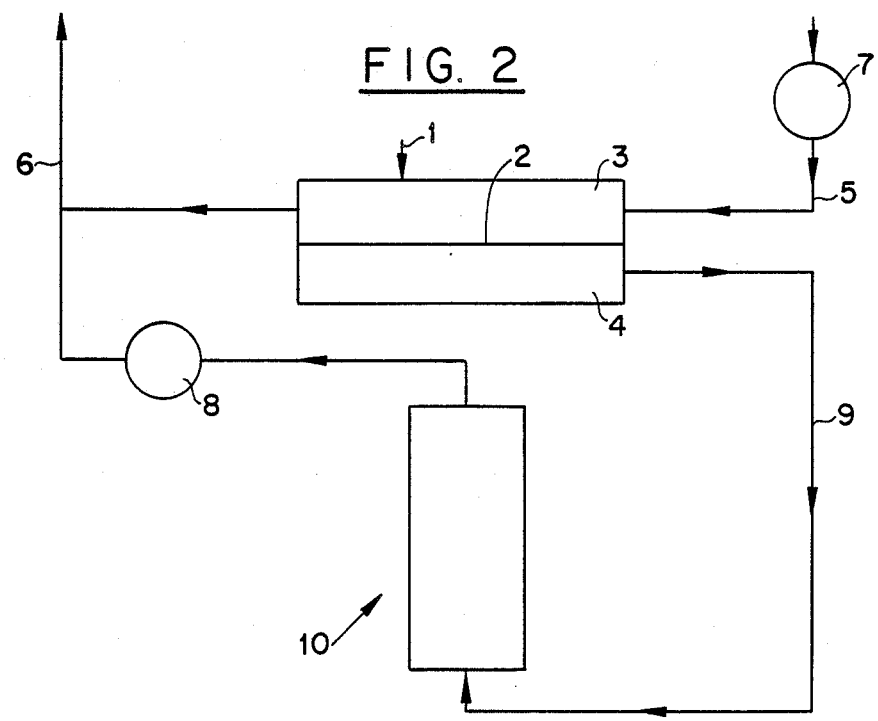

In FIG. 1 the numeral 1 refers to an artificial kidney which consists of two compartments separated by a selectively permeable membrane 2, viz. a blood compartment 3 and a dialysate compartment 4. The membrane may be in any form desired, for instance in the form of a flat or tubular film or consist of a great many hollow fibres. The blood compartment 3 can be connected to the circulatory system of a patient by means of blood tubes 5 and 6. Extracorporal transport of the blood may be assisted by a blood pump 7. Through the dialysate compartment 4 there is a flow of dialysis liquid which is caused to circulate through a dialysate circuit 9 by means of a dialysate pump 8. In the dialysate circuit there is a regeneration unit 10 which purifies the dialysis liquid from the waste products it has taken up from the blood in the dialysate compartment. The regeneration unit may consist of several parts connected in series or in parallel, which each serve to eliminate one or more waste products. Alternatively, the regeneration unit, or part of it, may contain a mixture of different sorbents. The regeneration unit contains a sorbent according to the invention. The sorbent may be rendered suitable for the sorption of various substances, so that the use of separate sorbents may be limited. It is conceivable to use a urea sorbent whose macromolecular matrix also has ion exchanging properties, as the one according to U.S. Pat. No. 4 213 859.

The phosphate sorbent described in it may, if appropriately pre-charged, take up $K^+$ in addition to phosphate and equilibrate the $Ca^{++}$ and $Mg^{++}$ concentrations.

In addition to being employed for hemodialysis the sorbent according to the invention may be used for the purification of dialysis liquid in peritoneal dialysis or in hemofiltration. In the latter case there is used an ultrafiltration device 1, as is shown in FIG. 2, comprising a blood compartment 3 separated by a membrane 2 from a filtration compartment 4. When the pressure prevailing in the blood compartment 3 is higher than in the filtration compartment 4, the membrane 2 will allow the passage of water containing low molecular weight waste products, such as urea, creatinine and uric acid, from the blood flowing through the compartment 3. This so-called ultrafiltrate is sucked out of the compartment 4 by a pump 8 and subsequently passes through the regeneration unit 10. This regeneration unit may be of the kind described with reference to FIG. 1. Upon leaving the regeneration unit 10 the purified ultrafiltrate joins the blood cells fraction before being fed back to the patient through the tube 6.

The sorbent according to the invention also may be used in hemoperfusion, i.e. the blood to be purified is directly passed through a column containing the sorbent. The sorbent may best be used in the form of particles of a size such that a favourable ratio between sorption rate and flow resistance is obtained. If necessary, the particles may be enveloped by a semipermeable wall.

The invention will be further illustrated in the following examples concerning the preparation of a few materials and their use as a sorbent. By % is meant percent by weight.

EXAMPLE I a. To 106 g of beads of a macroporous copolymer of 91.3% of styrene and 8.3% of technical 60%-divinyl benzene (apparent density: 0.55 g/ml; bead diameter: 0.3–0.8 mm), swollen in 1 liter of 1,2-dichloroethane there were added with stirring 139 g of propionyl chloride, followed by portionwise adding 320 g of ferric chloride over a period of 15 minutes. Subsequently, the mixture was stirred for 8 hours at 50° C. After the liquid layer had been drained the copolymer beads were successively washed with acetone, water and a 30%-hydrochloric acid solution to remove the iron salts. The resin prepared was freed of acid and subsequently dried in a vacuum desiccator.

b. The 181 g of propionylated resin obtained was introduced into a stirrer autoclave along with 240 ml of 25%-ammonia, 180 g of sulphur and 350 ml of pyridine. The Willgerodt reaction mixture was stirred for 10 hours at a temperature of 150° C. Next, the resin was washed with hot water and acetone, steamed out and again washed with water. After drying in the vacuum desiccator there were obtained 185 g of phenyl propionamide type of resin.

c. The resin prepared was hydrolysed for 24 hours with refluxing in a solution of 370 g of potassium hydroxide in 350 ml of water and 900 ml of ethanol. The resin was washed out with water and converted into a phenylpropionic acid type of resin by treatment with a 6% hydrochloric acid solution in a percolator column, followed by washing with water. After drying in a vacuum desiccator there were obtained 173 g of dry product.

d. The resin prepared was stirred in 1 liter of dichloroethane, after which 250 ml of thionyl chloride were added. The resulting mixture was stirred for 8 hours at 70° C., during which sulphur dioxide and hydrochloric acid gas escaped. Subsequently, the remaining thionyl chloride was removed in a column by percolation with dichloroethane in an amount equivalent to four times the resin volume. The resulting polymeric carboxylic acid chloride was introduced into 2 l of dichloroethane, followed by portionwise adding, with stirring, 250 g of anhydrous ferric chloride powder. Cyclization was carried out for 18 hours at 50° C. Subsequently, the 1-indanone type resin prepared was separated from the liquid layer and successively washed with acetone, water and a 30%-hydrochloric acid solution. Next, rests of solvent were removed from the resin with the aid of steam and the resin was again washed with water and dried in a vacuum dessicator. The resin yield was 182 g.

e. 50 g of the resin prepared were taken up in a mixture of 250 ml of dimethyl sulphoxide and 50 ml of 47%-hydrobromic acid solution. The mixture was then stirred for 18 hours at 90° C., with the dimethyl sulphide formed being distilled off. The distillate may be converted, if desired, into the sulphoxide with the aid of a hydrogen peroxide solution and used again. Next, the resin is washed out successively with methanol and water.

In an experiment on cell cultures the sorbent material was found to be non-toxic.

EXAMPLE II a. To 106 g of a macroporous copolymer of 95% styrene and 5% technical divinylbenzene (apparent density: 0.48 g/ml), swollen in 1100 ml of carbon disulphide there were added with stirring 162 g of propionyl chloride, followed by portionwise addition of 334 g of aluminium chloride over a period of 20 minutes. The mixture was refluxed, with stirring, for 18 hours. After draining the liquid the beads were washed with a 30% hydrochloric acid solution. The remaining solvent was steamed out and the product was washed free of acid and dried in a vacuum desiccator.

b. The 170 g of product obtained were introduced into a stirrer autoclave along with 270 ml of 25% ammonia, 140 g of sulphur and 420 ml of pyridine.

The mixture was stirred for 6 hours at 180° C.

After working-up as described in Example Ib, 188 g of product resulted.

c. The resin was hydrolysed by heating for 18 hours at 120° C. in a solution of 600 g of potassium hydroxide in 1200 ml of ethylene glycol monomethylether, with stirring.

After washing with ethanol the product was worked up further according to Example I.c. 176 g of dry propionic acid type resin were obtained.

d. The resin was stirred into 1200 ml of dichloro ethane and 240 ml of thionylchloride and 15 ml of pyridine were added. The mixture was stirred for 4 hours at 75° C. The product was worked-up and cyclized as described in Example I, with exception that 145 g of aluminium chloride were used instead of the ferric chloride powder.

e. 50 g of the resin obtained above were oxidized and worked-up as described in Example I.e.

EXAMPLE III a. To a mixture of 106 g of a macroporous copolymer of 88.3% of styrene and 11.7% of technical divinyl benzene (apparent density: 0.55 g/ml) and 1 liter of 1,2-dichloroethane there were added 160 g of β-chloropropionyl chloride and, portionwise, 210 g of anhydrous ferric chloride powder. The mixture was heated for 8 hours at 50° C., with stirring. After the liquid layer had been poured off, the copolymer beads were successively washed out with acetone, water and a 30%-hydrochloric acid solution. The remaining solvent was steamed out and the resin prepared freed of acid with the aid of water and subsequently dried in a vacuum dessicator.

b. The resulting 180 g of chloropropionylated resin were stirred up in a reactor in which 600 ml of nitrobenzene and 400 ml of 95% sulphuric acid were present. The mixture was heated to 80° C. for 18 hours, with stirring.

After the liquid layer had been poured off, the product prepared was washed with water, freed of nitrobenzene with the aid of steam and again washed with water. After drying in a vacuum dessicator there were obtained 172 g of 1-indanone type of product.

c. 50 g of the product thus prepared were subjected to a 24 hour oxidative treatment with selenium dioxide, as described in part b of Example VI.

EXAMPLE IV a. 106 g of a geltype copolymer of 98% styrene and 2% technical divinylbenzene were propionylated as described in Example I.a., with the exception that the propionylchloride was used in an amount of 122 g and 267 g of aluminium chloride, instead of the ferric chloride were used. The product was further treated as described in Example II.b. and c.

b. The phenylpropionic acid type resin obtained was taken up in 700 ml of dichloroethane to which 280 ml of oxalylchoride were added and stirred for 6 hours at 60° C. The product was worked-up further according to Example II.d. and e.

EXAMPLE V a. A condensate-type resin was prepared as follows:

A mixture of 43 ml of benzylchloride, 7 ml of p-xylylenedichloride and 50 ml of an alkane fraction having a boiling point of 140°-160° was stirred in a large vessel and a solution of 1.5 g of ferric chloride in 50 ml of nitrobenzene was added at once while the vessel was cooled in ice. After the initial reaction the product was heated for 3 hours at 80° C. The product was washed with acetone, crushed, then washed with water, 30% hydrochloric acid solution and again water. The dried product was crushed further and the 0.3–1.0 mm sieve fraction was collected.

b. 100 g of the above condensate type resin were subjected to the chemical conversions, described in Example IV.a and b.

EXAMPLE VI a. Example I was repeated, with the exception that use was made of 106 g of the macroporous copolymer of Example II, which was subjected to the chemical conversions as described in the parts a through d of Example I.

b. Of the resulting 179 g of 1-indanone type resin 50 g of dry resin were added, with stirring to a mixture of 500 ml of acetic acid and 25 ml of water. Subsequently, there were added, with stirring, 100 g of selenium dioxide powder, after which the mixture was heated for 18 hours with refluxing. Next, the resin was stirred up in water and washed out.

EXAMPLE VII a. In this example 106 g of the macroporous starting copolymer of Example VI were subjected to the chemical conversions as described in Example I, parts a through c.

b. The resulting 170 g of dry phenylpropionic acid type resin were mixed with 1500 g of polyphosphoric acid having a phosphorus pentoxide content of 85%. The resulting mixture was stirred for 18 hours at 140° C. under nitrogen. After successively washing with water, a hot 6% soda solution and again water, followed by drying in a vacuum dessicator there were obtained 184 g of 1-indanone type of resin.

c. 50 g of the resin thus prepared were oxidized with a mixture of dimethyl sulphoxide and hydrobromic acid, as described in part e of Example I.

EXAMPLE VIII a. A condensate-type resin of benzyl chloride and 25% of p-xylene dichloride was prepared according to Example V.a.

b. 100 g of this condensate resin were reacted with propionyl chloride according to Example IV.a. Then the series of reactions, described in Example II.b. through d. was carried out. Subsequently, the oxidative treatment of Example III.c. was applied.

EXAMPLE IX 50 g of a dry resin of the type 1-indanone prepared according to the Exs. I.a through I.d, were introduced into 250 ml of 96%-$H_2SO_4$ and heated for 20 hours at 50° C. After cooling the reaction mixture was slowly poured into an ice-water mixture. The resin was washed out with water and subsequently dried. The resulting resin contained 1,1 meq sulphonic acid groups per gramme.

The resin was oxidized for 24 hours with HBr/DMSO and further treated as described in Example I.e. The endproduct displayed increased capacity for $K^+$ removal and buffering of the $Ca^{++}$ and the $Mg^{++}$ levels.

EXAMPLE X 50 g of a copolymer of 90% p-vinylbenzoylacetone and 10% technical divinyl benzene were added with stirring to a mixture of 800 ml of glacial acetic acid and 20 ml of water. Subsequently, 44 g of selenium dioxide were added and the mixture was stirred for 16 hours at 80° and then refluxed for 16 hours. The resulting product was stirred up in water and washed out.

EXAMPLE XI a. 10 g of a copolymer of 90% methacroylacetone and 10% technical divinylbenzene were swollen in 160 ml of dioxane and 4 ml of water. 13 g of selenium dioxide were added and the mixture was stirred for 16 hours at 80° C. and then refluxed for 16 hours.

The product was stirred up in water and washed out.

EXAMPLE XII 80 g of a macroporous polymer of technical 60%-divinyl benzene having a surface area of 740 $m^2/g$ and an apparent density of 0.50 g/ml were suspended in 500 ml of water, followed by adding 20 g of ninhydrin at a temperature of 50° C. After 6 hours' stirring the mixture was cooled with stirring and the polymer washed out with water and dried. The resulting product contained 20% by weight of ninhydrin.

Experiments

The sorbents prepared in the Examples I–XI were used to carry out experiments in vitro to determine the urea and ammonia sorption. To that end dialysis liquids A and B were prepared.

The dialysis liquid A was composed as follows:

| | | | | |
|---|---|---|---|---|
| $Na^+$ | 140 | meq/l | glucose | 2 g/l |
| $K^+$ | 4 | meq/l | urea | 2 g/l |
| $Ca^{2+}$ | 3,5 | meq/l | creatinine | 0,15 g/l |
| $Mg^{2+}$ | 1,0 | meq/l | uric acid | 0,15 g/l |
| $Cl^-$ | 112,5 | meq/l | | |
| $HCO_{32-}^-$ | 40 | meq/l | | |
| $HPO_{42-}$ | 4 | meq/l | pH set to 7,4/ | |
| | | | temp. 37° C. | |
| $SO_4$ | 2 | meq/l | | |

This dialysis liquid served for the determination of the urea take up.

The dialysis liquid B had the same composition as the dialysis liquid A, except that instead of urea, ammonium carbonate was used in a concentration such that per liter of dialysis liquid 1.13 g of $NH_3$ was present. The products obtained according to the Examples I through V were buffered by percolation with a 4% sodium bicarbonate solution which had been brought to a pH of 7.4 with acid. Subsequently, these products were percolated with a pH=7.4 solution of 140 meq/l sodium chloride, 3.5 meq/l calcium chloride and 1 meq/l magnesium chloride and subsequently washed shortly with demineralized water. After addition of the products thus treated to the dialysis liquids A and B their pH and their $Ca^{2+}$ and $Mg^{2+}$ levels were found to have hardly changed. In the evaluation of the take-up results a correction was made for the water content of the products used. The sorbents were used in amounts such that the urea and the ammonia levels of the dialysis liquids A and B, respectively, dropped to about 0.5 g/l and 0.25 g/l, respectively, after the addition of the products of the Examples I through V.

The experiments were carried out in stirred vessels, closed off from their environment and thermostatted at 37° C. The pH of the liquid was monitored.

The urea analyses were carried out spectrophotometrically both by the D.A.M. method (diacetyl monoxime+ferric ion+sulphuric acid/phosphoric acid mixture, gives red colour) and the Berthelot method (urease converts urea into $NH_3$, which used with hypochlorite gives indophenol blue).

The results obtained were identical. Ammonia was determined using the colour reaction of the Berthelot method.

Test results for the products obtained in the Examples I through XI

The results of the urea sorption experiments are given in Table 1, those of the ammonia sorption experiments in Table 2.

TABLE 1

| | Urea sorption tests | |
|---|---|---|
| | | Sorption level |
| Product | | g urea/kg dry product |
| of | after | |
| Example | 6 h | at equilibrium |
| I | 24 | 101 |

TABLE 1-continued

Urea sorption tests

| Product of Example | Sorption level g urea/kg dry product | |
|---|---|---|
| | after 6 h | at equilibrium |
| II | 42 | 123 |
| III | 17 | 67 |
| IV | 22 | 108 |
| V | 23 | 80 |
| VI | 25 | 114 |
| VII | 19 | 82 |
| VIII | 24 | 86 |
| IX | 25 | 83 |
| X | 6 | 10 |
| XI | 7 | 12 |

In the above tests with products of Examples II, IV and V the creatinine level was also analysed. All these sorbents were found to lower the level by 70–80%.

TABLE 2

Ammonia sorption tests

| Product of Example | Sorption level $NH_3$/kg dry product | |
|---|---|---|
| | after 1 h | at equilibrium |
| I | 22 | 37 |
| II | 27 | 39 |
| III | 16 | 23 |
| IV | 21 | 33 |
| VII | 18 | 30 |
| VIII | 23 | 34 |
| IX | 13 | 16 |

Test result product XII

The product obtained in Example XII was subjected to a column test: 2 l of the liquid A were circulated through a column (2 cm) at a rate of 1 l/h, the column being filled with a sublayer of uncharged porous polymer of Example XII (corresponding to 10 g of dry matter, to prevent leaking down of ninhydrin) on which there was provided a layer of the product of Example XII (corresponding to 50 g of dry matter). When it had reached the state of equilibrium, the last-mentioned product had taken up 24 g urea/kg of dry product.

The above-described specific methods of preparing the material also may be used for the preparation of a low molecular weight compound with a polycarbonyl unit, more particularly ninhydrin. More particularly, the halogen acid/dialkyl sulphoxide oxidation or the halogenation followed by dialkyl sulphoxide treatment are applied to the monocarbonyl compounds 1-indanone and 2-indanone. These two last-mentioned compounds may be obtained by the above-described methods of preparation or, for instance, by conversion of the relatively inexpensive indene with HCl followed by oxidation (Org. Synth. Coll., Vol. II, p. 336), respectively with formic acid and hydrogen peroxide, followed by steam distillation in the presence of sulphuric acid (Org. Synth. Coll., Vol. V, p. 646). This direct preparation of ninhydrin by oxidation of a monocarbonyl compound with HBr/DMSO (hydrobromic acid/dimethyl sulphoxide), or by bromination followed by treatment with DMSO, is a simpler procedure than the previously described ninhydrin syntheses.

Many equivalent modifications will become apparent to those skilled in the art from a reading of the above specification without a departure from the inventive concept therein.

I claim:

1. A method for the extracorporeal clinical removal of ammonia, urea, creatinine, or other waste products having one or more amino groups, from blood or blood serum, comprising contacting said blood or blood serum with a cross-linked copolymer of a monovinyl aromatic compounds and a polyvinyl aromatic compound, said cross-linked copolymer having groupings containing three vicinal carbonyl groups or a hydrate thereof, followed by removal of said blood or blood serum from contact with said material.

2. The method of claim 1, wherein the polyvinyl aromatic compound is divinyl benzene.

3. The method of claim 2, wherein the material contains 0.1–90% by weight of divinyl benzene.

4. A method for the extracorporeal clinical removal of ammonia, urea, creatinine, or other waste products having one or more amino groups, from blood or blood serum, comprising contacting said blood or blood serum with a copolymer of styrene and 0–90% by weight of divinyl benzene with 5 carbon atoms-containing rings having three vicinal carbonyl groups or a hydrate thereof covalently bonded to said copolymer.

5. The method of claim 4, wherein the copolymer of styrene is a macroporous copolymer comprising 0.1–90% by weight of divinyl benzene.

* * * * *